United States Patent
Koshiba

(10) Patent No.: US 10,561,350 B2
(45) Date of Patent: Feb. 18, 2020

(54) ENDOSCOPE SYSTEM, PROCESSOR DEVICE OF ENDOSCOPE SYSTEM, AND METHOD OF OPERATING ENDOSCOPE SYSTEM

(71) Applicant: FUJIFILM Corporation, Tokyo (JP)

(72) Inventor: Masaaki Koshiba, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 479 days.

(21) Appl. No.: 15/280,038

(22) Filed: Sep. 29, 2016

(65) Prior Publication Data

US 2017/0014059 A1    Jan. 19, 2017

Related U.S. Application Data

(63) Continuation of application No. PCT/JP2015/058898, filed on Mar. 24, 2015.

(30) Foreign Application Priority Data

Mar. 31, 2014   (JP) .................................. 2014-074268

(51) Int. Cl.
*A61B 5/1455* (2006.01)
*A61B 1/04* (2006.01)
(Continued)

(52) U.S. Cl.
CPC .......... *A61B 5/14552* (2013.01); *A61B 1/043* (2013.01); *A61B 1/045* (2013.01);
(Continued)

(58) Field of Classification Search
CPC ..... A61B 5/14552; A61B 1/045; A61B 1/043; A61B 1/051; A61B 1/018; A61B 1/126;
(Continued)

(56) References Cited

U.S. PATENT DOCUMENTS 9,826,891 B2 * 11/2017 Kagaya .................. A61B 1/051
2008/0239070 A1 * 10/2008 Westwick .............. A61B 1/045
348/68

(Continued)

FOREIGN PATENT DOCUMENTS

EP    2 229 870 A1    9/2010
EP    2 476 373 A1    7/2012
(Continued)

OTHER PUBLICATIONS

Extended European Search Report, dated Apr. 18, 2017, for European Application No. 15772409.7.
(Continued)

*Primary Examiner* — Sanjay Cattungal
(74) *Attorney, Agent, or Firm* — Birch, Stewart, Kolasch & Birch, LLP

(57) ABSTRACT

Provided is an endoscope system capable of improving luminance and an S/N ratio of a normal observation image that is obtained in a special observation mode.
In a special observation mode, after first illumination light is radiated, some of a plurality of pixel rows of an imaging element are reset en bloc. Illumination light is switched to second illumination light, the second illumination light is radiated, and then, a turned-off state is reached. During this turn-off period, signal reading is sequentially performed from all pixel rows. An image processing unit generates a normal observation image on the basis of a first imaging signal without being subjected to resetting. Further, the image processing unit generates an oxygen saturation image on the basis of a second imaging signal read from the pixel row subjected to the resetting and exposed by only the second illumination light, and the first imaging signal.

11 Claims, 15 Drawing Sheets

(51) Int. Cl.
*A61B 1/045* (2006.01)
*A61B 1/05* (2006.01)
*G02B 5/20* (2006.01)
*G02B 23/24* (2006.01)
*A61B 1/018* (2006.01)
*A61B 1/12* (2006.01)

(52) U.S. Cl.
CPC .............. *A61B 1/051* (2013.01); *G02B 5/201* (2013.01); *G02B 23/2461* (2013.01); *A61B 1/018* (2013.01); *A61B 1/041* (2013.01); *A61B 1/126* (2013.01)

(58) Field of Classification Search
CPC .... A61B 1/041; G02B 5/201; G02B 23/2461; G03B 15/05; G03B 37/005; G03B 33/02
See application file for complete search history.

(56) References Cited

U.S. PATENT DOCUMENTS

| | | | |
|---|---|---|---|
| 2009/0147077 A1* | 6/2009 | Tani | A61B 1/042 348/68 |
| 2009/0149705 A1* | 6/2009 | Tani | A61B 1/05 600/109 |
| 2010/0194938 A1* | 8/2010 | Iwasa | H04N 5/2353 348/266 |
| 2010/0240953 A1* | 9/2010 | Murakami | A61B 1/0005 600/109 |
| 2012/0016201 A1* | 1/2012 | Seto | A61B 1/045 600/180 |
| 2013/0208101 A1* | 8/2013 | Ono | A61B 1/00193 348/65 |
| 2014/0046131 A1* | 2/2014 | Morita | A61B 1/00179 600/109 |
| 2014/0078277 A1* | 3/2014 | Dai | A61B 1/00004 348/68 |
| 2014/0100427 A1 | 4/2014 | Saito et al. | |
| 2014/0225998 A1* | 8/2014 | Dai | H01L 27/14601 348/65 |
| 2016/0213238 A1* | 7/2016 | Adachi | H04N 5/361 |

FOREIGN PATENT DOCUMENTS

| | | |
|---|---|---|
| EP | 2 550 910 A1 | 1/2013 |
| JP | 2010-68992 A | 4/2010 |
| JP | 2013-13656 A | 1/2013 |

OTHER PUBLICATIONS

International Search Report, issued in PCT/JP2015/058898, PCT/ISA/210, dated Jun. 23, 2015.
Written Opinion of the International Searching Authority, issued in PCT/JP2015/058898, PCT/ISA/210, dated Jun. 23, 2015.

* cited by examiner

ENDOSCOPE SYSTEM, PROCESSOR DEVICE OF ENDOSCOPE SYSTEM, AND METHOD OF OPERATING ENDOSCOPE SYSTEM

CROSS-REFERENCE TO RELATED APPLICATION

This application is a Continuation of PCT International Application PCT/JP2015/058898 filed on 24 Mar. 2015, which claims priority under 35 USC 119(a) from Japanese Patent Application No. 2014-074268 filed on 31 Mar. 2014. The above application is hereby expressly incorporated by reference, in its entirety, into the present application.

BACKGROUND OF THE INVENTION

1. Field of the Invention

The present invention is an endoscope system having a special observation mode, a processor device of the endoscope system, and a method of operating the endoscope system.

2. Description of the Related Art

In the medical field, for example, diagnosis using an endoscope system comprising a light source device, an endoscope, and a processor device has been widely performed. The endoscope system includes an endoscope system having a special observation mode in which an observation part inside a living body is irradiated with first illumination light and second illumination light having different spectral characteristics and observation is performed.

In the special observation mode, the first illumination light and the second illumination light are alternately supplied from the light source device to the endoscope, and an observation part is irradiated with the light from a distal end portion of the endoscope. For example, the first illumination light is white light (normal light), and the second illumination light is special light including light for which blood hemoglobin has a high light absorption coefficient. A normal observation image is generated by imaging an observation part illuminated by the first illumination light, and a special observation image is generated by imaging the observation part illuminated by the second illumination light.

In an endoscope system of the related art, a charge coupled device (CCD) type imaging element is used as an imaging element of an endoscope, whereas in recent years, a complementary metal-oxide semiconductor (CMOS) type imaging element is used (see JP2010-68992A). This is because the CMOS type imaging element has lower power consumption than the CCD type imaging element or peripheral circuits such as an analog-to-digital converter (ADC) circuit can be formed on the same substrate as that for the imaging unit. In this CMOS type imaging element, basically, a rolling shutter scheme in which resetting and signal reading are performed sequentially pixel row by pixel row for a plurality of pixel rows configured in the imaging unit is adopted. A period from the resetting of each pixel row to signal reading is an exposure period.

Since an exposure timing is shifted sequentially pixel row by pixel row in the rolling shutter scheme, assuming that illumination light is switched from the first illumination light to the second illumination light without interruption while driving the imaging element in the rolling shutter scheme, an exposure period of some pixel rows straddles switching of the illumination light, and a combination of the first illumination light and the second illumination light is imaged. Therefore, JP2010-68992A proposes that a turn-off period is provided in the event that the illumination light is switched, and signal reading is performed during this turn-off period.

As described above, assuming that a turn-off period is simply provided in the event that first illumination light and second illumination light are switched, a frame rate of the imaging element is decreased due to the turn-off period. Therefore, in JP2010-68992A, a decrease in the frame rate is prevented by shortening each irradiation time (exposure time) of the first and second illumination light and shortening a reading time by decimating the number of pixels on which signal reading is performed from the imaging element.

However, in the endoscope system described in JP2010-68992A, first illumination light is radiated at all times and the imaging element is driven in a rolling shutter scheme in a normal observation mode. However, in a special observation mode, since an exposure time is shortened so that the frame rate is not decreased, there is a problem in that luminance and a signal-to-noise (S/N) ratio are decreased in a normal observation image obtained in the special observation mode in comparison with a normal observation image obtained in the normal observation mode.

SUMMARY OF THE INVENTION

An object of the present invention is to provide an endoscope system capable of improving luminance and an S/N ratio of a normal observation image that is obtained in a special observation mode, a processor device of the endoscope system, and a method of operating the endoscope system.

To achieve the above object, an endoscope system of the present invention comprises an illumination unit, an endoscope, a control unit, and an image processing unit. The illumination unit irradiates a specimen with first and second illumination light having different spectral characteristics. The endoscope includes a CMOS type imaging element that images the specimen illuminated by the illumination unit using a plurality of pixel rows arranged in a column direction. The control unit causes the illumination unit and the imaging element to execute a first imaging scheme for resetting some of the plurality of pixel rows en bloc after the specimen is irradiated with the first illumination light from the illumination unit, turning off the illumination unit after the specimen is irradiated with the second illumination light from the illumination unit, and performing signal reading from all of the pixel rows. The image processing unit generates a normal observation image on the basis of a first imaging signal read from the pixel row exposed by the first and second illumination light without being subjected to the resetting, and generates a special observation image on the basis of a second imaging signal read from the pixel row at least subjected to the resetting and exposed by only the second illumination light.

The imaging element can include a color filter array in a Bayer array. In this case, it is preferable that the control unit performs the resetting on a half of the plurality of pixel rows.

The first illumination light or the second illumination light can include different light absorption wavelength light for which a light absorption coefficient differs between oxygenated hemoglobin and deoxygenated hemoglobin. In this case, it is preferable that the image processing unit generates an oxygen saturation image including information on oxygen saturation as the special observation image.

It is preferable that the image processing unit calculates the oxygen saturation on the basis of the first and second imaging signals, and performs image processing on the normal observation image on the basis of the oxygen saturation to generate the oxygen saturation image.

It is preferable that the control unit causes the illumination unit and the imaging element to execute a second imaging scheme for turning off the illumination unit and performing signal reading after the specimen is irradiated with the first illumination light from the illumination unit, and turning off the illumination unit and performing signal reading after the specimen is irradiated with the second illumination light from the illumination unit.

It is preferable that the control unit performs the signal reading after the irradiation of the first illumination light, and then, radiates the second illumination light without resetting any of the plurality of pixel rows at the time of execution of the second imaging scheme.

It is preferable that the control unit performs the signal reading from some of the plurality of pixel rows through decimation reading at the time of execution of the second imaging scheme. In this case, it is preferable that the control unit changes the pixel row on which the decimation reading is performed through signal reading after irradiation of the first illumination light and signal reading after irradiation of the second illumination light.

The endoscope system comprises a brightness detection unit that detects brightness of the specimen. In this case, it is preferable that the control unit causes the first imaging scheme to be executed in a case in which the brightness is smaller than a certain value, and the second imaging scheme to be executed in a case in which the brightness is equal to or greater than a certain value.

A processor device of an endoscope system of the present invention comprises a control unit and an image processing unit. The control unit causes the illumination unit and the imaging element to execute a first imaging scheme for resetting some of the plurality of pixel rows en bloc after the specimen is irradiated with the first illumination light from the illumination unit, turning off the illumination unit after the specimen is irradiated with the second illumination light from the illumination unit, and performing signal reading from all of the pixel rows. The image processing unit generates a normal observation image on the basis of a first imaging signal read from the pixel row exposed by the first and second illumination light without being subjected to the resetting, and generates a special observation image on the basis of a second imaging signal read from the pixel row at least subjected to the resetting and exposed by only the second illumination light.

A method of operating an endoscope system of the present invention comprises a first step and a second step. In the first step, a control unit causes an illumination unit and an imaging element to execute a first imaging scheme for resetting some of the plurality of pixel rows en bloc after the specimen is irradiated with the first illumination light from the illumination unit, turning off the illumination unit after the specimen is irradiated with the second illumination light from the illumination unit, and performing signal reading from all of the pixel rows. The second step includes generating a normal observation image on the basis of a first imaging signal read from the pixel row exposed by the first and second illumination light without being subjected to the resetting, and generating a special observation image on the basis of a second imaging signal read from the pixel row at least subjected to the resetting and exposed by only the second illumination light.

According to the present invention, in the special observation mode, since some of the plurality of pixel rows are reset en bloc after the imaging element is exposed by the first illumination light, the illumination unit is turned off after the imaging element is exposed by the second illumination light, signal reading is performed from all of the pixel rows, the normal observation image is generated on the basis of the first imaging signal read from the pixel row exposed by the first and second illumination light without being subjected to the resetting, and the special observation image is generated on the basis of the second imaging signal read from the pixel row at least subjected to the resetting and exposed by only the second illumination light, it is possible to improve luminance and an S/N ratio of the normal observation image that is obtained in the special observation mode.

DESCRIPTION OF THE PREFERRED EMBODIMENTS

Figure 1:
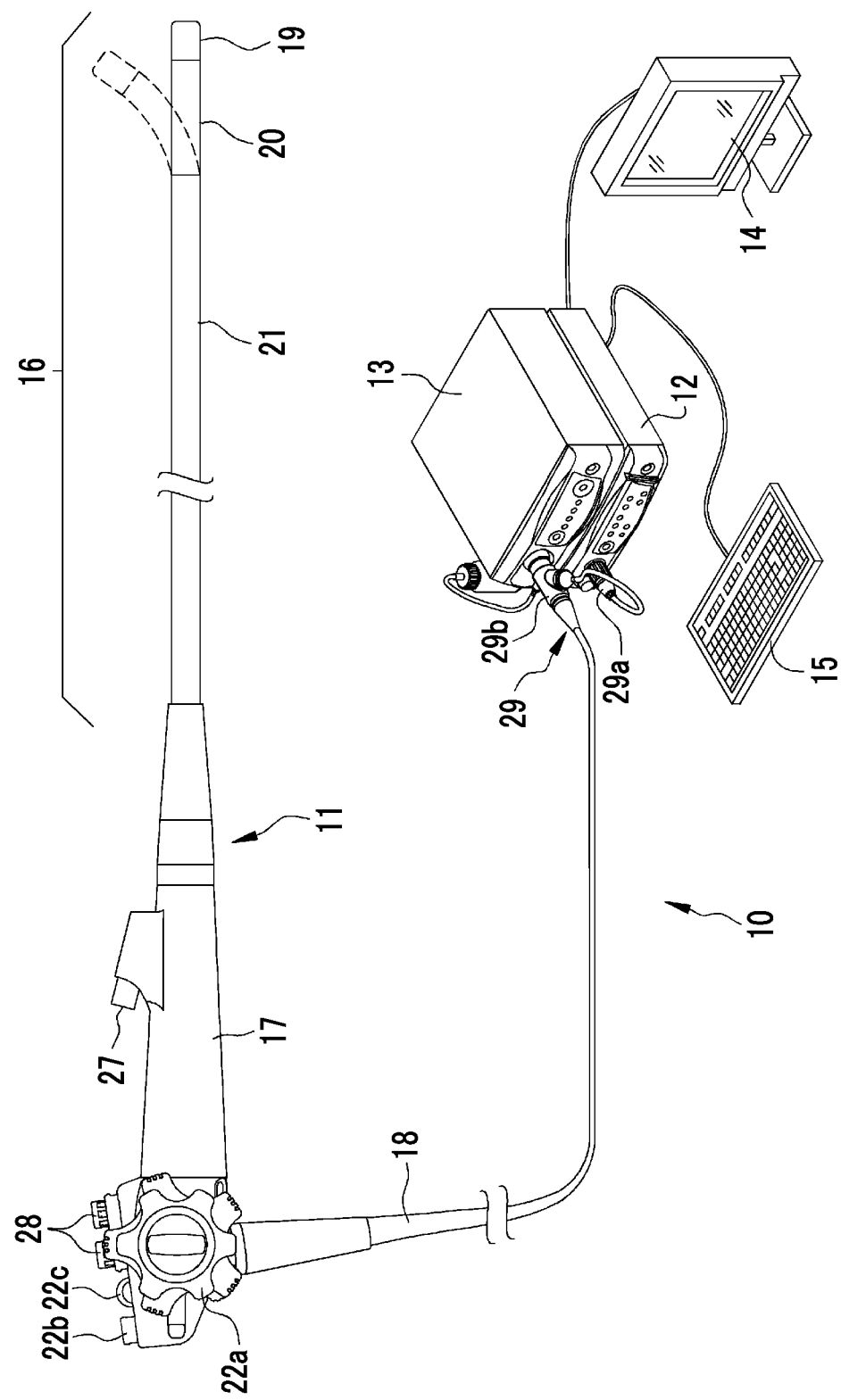
FIG. 1 is an external view of an endoscope system.

In FIG. 1, an endoscope system 10 includes an endoscope 11 that images an observation part (specimen) inside a body, a processor device 12 that generates a display image of the observation part on the basis of an imaging signal obtained by imaging, a light source device 13 that supplies illumination light with which the observation part is irradiated, to the endoscope 11, and a monitor 14 that displays a display image. In addition to the monitor 14, an input unit 15 such as a keyboard or a mouse is connected to the processor device 12.

The endoscope 11 includes an insertion part 16 that is inserted into a digestive tract of a living body, an operation portion 17 provided on a base end portion of the insertion part 16, and a universal cord 18 for connecting the endoscope 11 to the processor device 12 and the light source device 13. The insertion part 16 includes a distal end portion 19, a bending portion 20, and a flexible tube portion 21, which are connected in this order from the distal end side.

In angle knob 22a, a mode changeover switch 22b, and the like are provided in the operation portion 17. The angle knob 22a is used for an operation for bending the bending portion 20. Through the operation of the angle knob 22a, the distal end portion 19 can be directed in a desired direction.

The mode changeover SW 22b is used for a switching operation between two types of observation modes including a normal observation mode and a special observation mode. The normal observation mode is a mode in which a normal observation image obtained by imaging an observation target in full color using white light is displayed on the monitor 14. The special observation mode is a mode in which oxygen saturation of blood hemoglobin of the observation target is obtained, and an oxygen saturation image obtained by performing image processing on a normal observation image on the basis of the oxygen saturation is display on the monitor 14.

Figure 2:
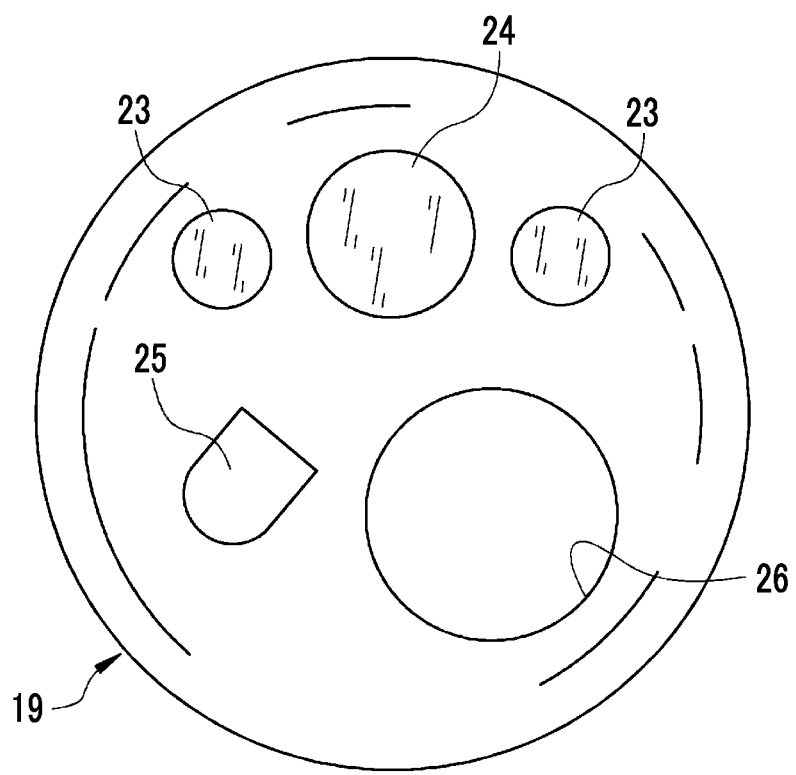
FIG. 2 is a front view of a distal end portion of an endoscope.

In FIG. 2, an illumination window 23 that irradiates an observation part with illumination light, an observation window 24 for capturing an image of the observation part, an air supply and water supply nozzle 25 that performs air supply and water supply in order to clean the observation window 24, and a forceps outlet 26 for performing various treatments by causing a treatment tool such as forceps or an electric scalpel to protrude are provided in a distal end surface of the distal end portion 19. An imaging element 39 (see FIG. 3) is built into an inner side of the observation window 24.

The bending portion 20 includes a plurality of coupled bending pieces, and is bent vertically and horizontally according to an operation of the angle knob 22a of the operation portion 17. By bending the bending portion 20, the distal end portion 19 is directed in a desired direction. The flexible tube portion 21 is flexible and can be inserted into a meandering tube passage such as an esophagus or intestines. A signal cable that transfers a control signal for driving the imaging element 39 or an imaging signal output by the imaging element 39, or a light guide 35 (see FIG. 3) that guides the illumination light supplied from the light source device 13 to the illumination window 23 is inserted into the insertion part 16.

In addition to the angle knob 22a and the mode changeover switch 22b, for example, a forceps port 27 for inserting the treatment tool, an air supply and water supply button 28 that is operated in the event that the air supply and water supply are performed from the air supply and water supply nozzle 25, and a freeze button (not illustrated) for capturing a still image are provided in the operation portion 17.

A communication cable or the light guide 35 extending from the insertion part 16 is inserted into the universal cord 18, and a connector 29 is attached to one end of the processor device 12 and the light source device 13. The connector 29 is a composite type connector including a communication connector 29a and a light source connector 29b. The communication connector 29a and the light source connector 29b are detachably connected to the processor device 12 and the light source device 13. One end of the communication cable is arranged in the communication connector 29a. An incident end 35a (see FIG. 3) of the light guide 35 is arranged in the light source connector 29b.

Figure 3:
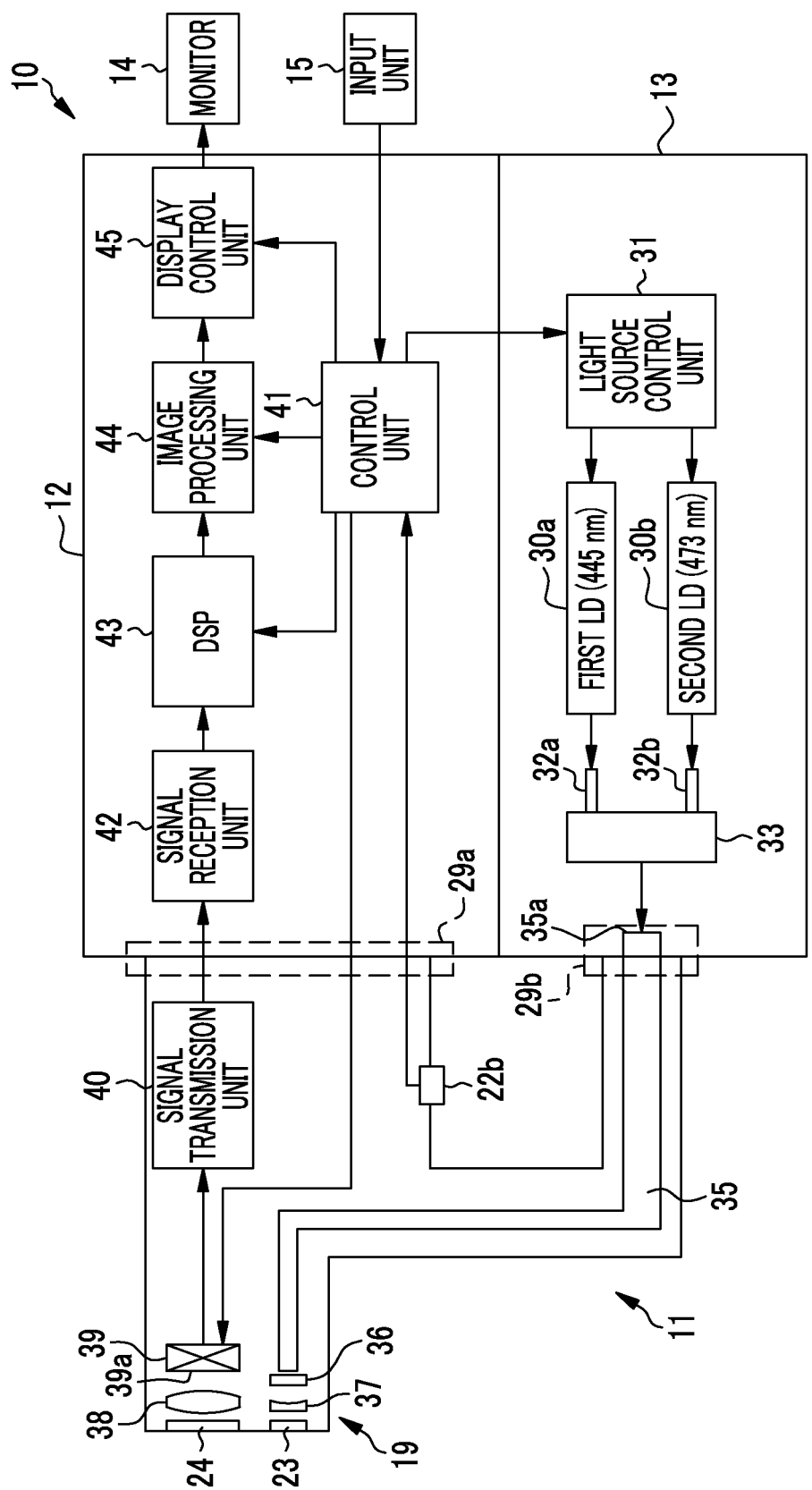
FIG. 3 is a block diagram illustrating an electric configuration of the endoscope system.

In FIG. 3, the light source device 13 includes first and second laser diodes (LDs) 30a and 30b, a light source control unit 31, first and second optical fibers 32a and 32b, and an optical coupler 33. The first LD 30a emits first blue laser light having a central wavelength of 445 nm. The second LD 30b emits second blue laser light having a center wavelength of 473 nm. Each of half-widths of the first and second blue laser light is about ±10 nm. For the first and second LDs 30a and 30b, a broad area type of InGaN-based laser diode, InGaNAs-based laser diode, GaNAs-based laser diode, or the like may be used.

The light source control unit 31 individually controls ON and OFF of the first and second LDs 30a and 30b. The light source control unit 31 turns on the first LD 30a in the normal observation mode. In the special observation mode, the light source control unit 31 sequentially turns on the first LD 30a and the second LD 30b.

The first blue laser light emitted from the first LD 30a is incident on the first optical fiber 32a. The second blue laser light emitted from the second LD 30b is incident on the second optical fiber 32b. The first and second optical fibers 32a and 32b are connected to the optical coupler 33. The optical coupler 33 integrates optical paths of the first and second optical fibers 32a and 32b and causes each of the first and second blue laser light to be incident on an incident end 35a of the light guide 35 of the endoscope 11.

The endoscope 11 includes the light guide 35, a phosphor 36, an illumination optical system 37, an imaging optical system 38, an imaging element 39, and a signal transmission unit 40. One light guide 35 is provided for each illumination window 23. As the light guide 35, a multi-mode fiber may be used. For example, a small-diameter fiber cable with a core diameter of 105 µm, a cladding diameter of 125 µm, and a diameter including a protective layer serving as an outer skin of 0.3 to 0.5 mm may be used.

In the event that the light source connector 29b is connected to the light source device 13, the incident end 35a of the light guide 35 arranged in the light source connector 29b faces an emitting end of the optical coupler 33. The phosphor 36 is arranged to face the emitting end of each light guide 35 located in the distal end portion 19. The first blue laser light or the second blue laser light is incident on the phosphor 36 via the light guide 35.

The phosphor 36 is a phosphor in which a plurality of types of fluorescent substances (for example, a phosphor such as a YAG-based phosphor or a BAM ($BaMgAl_{10}O_{17}$)) are dispersed in a binder to be in a rectangular parallelepiped shape. The phosphor 36 is excited by absorbing a part of the laser light (the first blue laser light or the second blue laser light) incident from the light guide 35, and emits fluorescence having a wavelength range from green to red. Further, a part of the laser light incident on the phosphor 36 is not absorbed by the phosphor 36 and passes through the phosphor 36 as it is. Accordingly, fluorescence and a part of the laser light are emitted from the phosphor 36.

Figure 4:
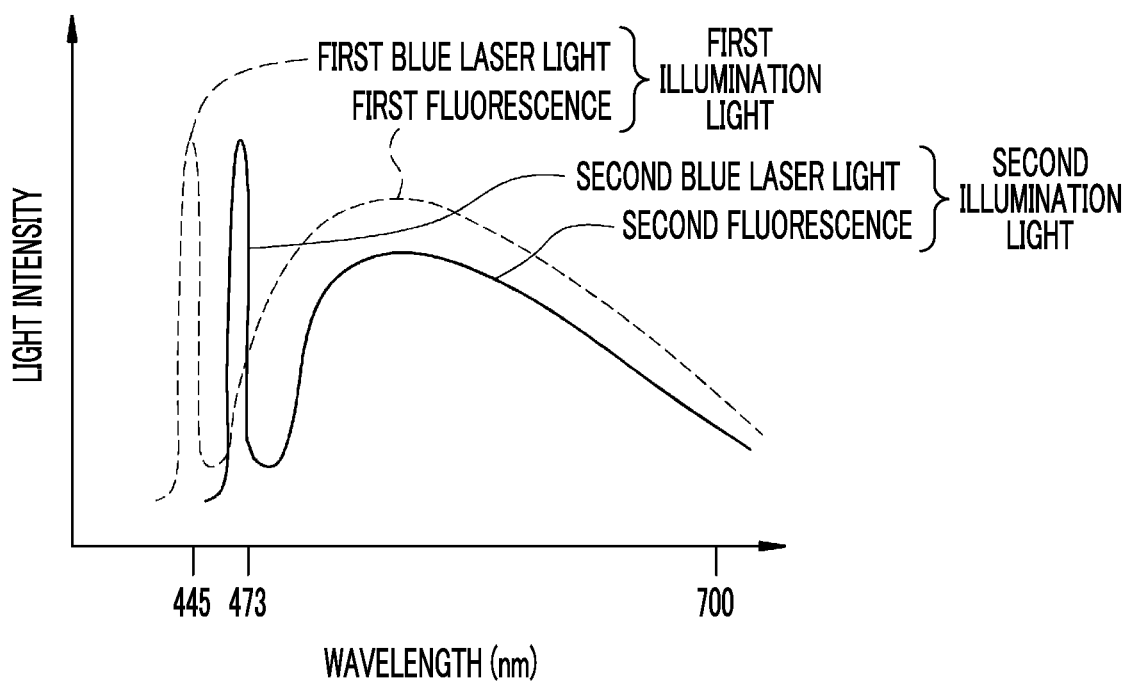
FIG. 4 is a graph illustrating an intensity spectrum of first and second illumination light.

Specifically, in a case in which the first LD 30a is turned on and the first blue laser light is incident on the phosphor 36, first illumination light having a spectrum illustrated in FIG. 4 is emitted from the phosphor 36. The first illumination light includes the first blue laser light, and the first fluorescence excited and emitted from the phosphor 36 by the first blue laser light. Further, in a case in which the second LD 30b is turned on and the second blue laser light is incident on the phosphor 36, second illumination light having the spectrum illustrated in FIG. 4 is emitted from the phosphor 36. The second illumination light includes the second blue laser light, and the second fluorescence excited and emitted from the phosphor 36 by the second blue laser light, and has spectral characteristics different from the first illumination light. Spectral shapes of the first fluorescence and the second fluorescence are substantially the same. That is, a ratio between an intensity ($\lambda$) of the first fluorescence and an intensity $I_2$ ($\lambda$) of the second fluorescence at a wavelength $\lambda$ are substantially constant.

The first and second illumination light emitted from the phosphor 36 is condensed by the illumination optical system 37 and radiated to an observation part inside a living body through the illumination window 23. Reflected light from the observation part is incident on the imaging optical system 38 through the observation window 24 and formed as an image on an imaging surface 39a of the imaging element 39 by the imaging optical system 38. In this embodiment, the light source device 13, the light guide 35, the phosphor 36, and the illumination optical system 37 correspond to an illumination unit described in claims.

The imaging element 39 is a CMOS type, and images the reflected light from the observation part to output an imaging signal on the basis of an imaging control signal supplied from the processor device 12.

The signal transmission unit 40 transmits the imaging signal obtained by the imaging element 39 to the processor device 12 in a known low-voltage operation signaling transmission scheme. Further, in the event that the above-described mode changeover switch 22b provided in the endoscope 11 is operated, a mode switching operation signal from the mode changeover switch 22b is transmitted to the processor device 12.

The processor device 12 includes a control unit 41, a signal reception unit 42, a digital signal processing unit (DSP: Digital Signal Processor) 43, an image processing unit 44, and a display control unit 45. The control unit 41 performs control of each unit in the processor device 12 and control of the imaging element 39 of the endoscope 11 and the light source control unit 31 of the light source device 13.

The signal reception unit 42 receives the imaging signal transmitted from the signal transmission unit 40 of the endoscope 11. The DSP 43 performs signal processing such as a defect correction process, a gain correction process, white balance processing, gamma conversion, or a demosaicing process on the imaging signal received by the signal reception unit 42.

In the normal observation mode, the image processing unit 44 performs, for example, a color conversion process, a color enhancement process, or a structure enhancement process on the imaging signal obtained by the imaging element 39 imaging the reflected light from the observation part irradiated with the first illumination light and subjected to the signal processing by the DSP 43 to generate a normal observation image.

Further, in the special observation mode, the image processing unit 44 calculates the oxygen saturation on the basis of the imaging signal obtained by the imaging element 39 imaging the reflected light from the observation part irradiated with the first and second illumination light and subjected to the signal processing by the DSP 43, calculates the normal observation image, and performs image processing on this normal observation image on the basis of the oxygen saturation to generate an oxygen saturation image (a special observation image) including information on the oxygen saturation.

The display control unit 45 converts an image generated by the image processing unit 44 into a signal in a display format and displays the signal on the monitor 14.

Figure 5:
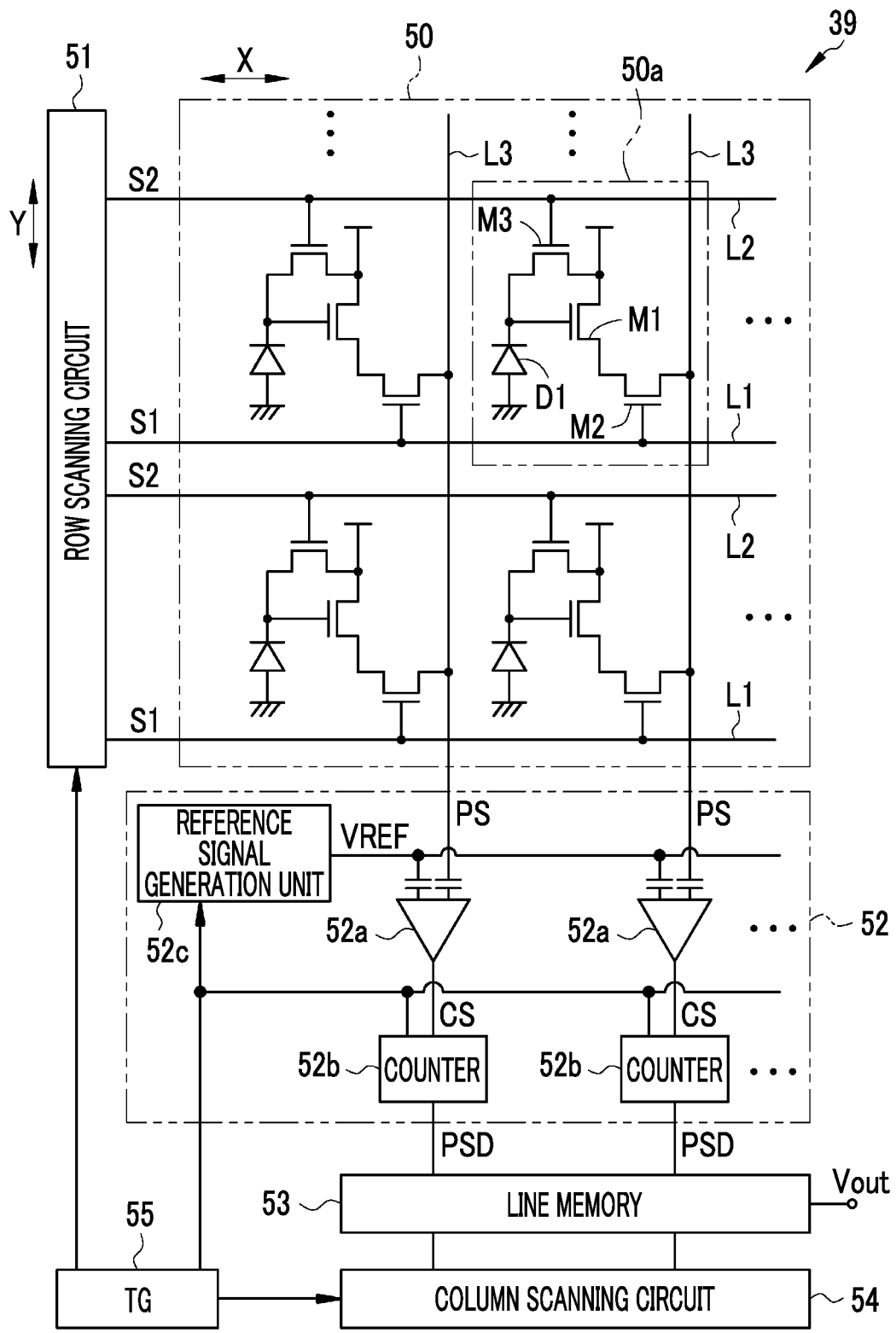
FIG. 5 is a diagram illustrating an electric configuration of an imaging element.

In FIG. 5, the imaging element 39 includes a pixel array unit 50, a row scanning circuit 51, a column ADC circuit 52 in which a plurality of analog-to-digital converters (ADCs) are arranged in a row direction, a line memory 53, a column scanning circuit 54, and a timing generator (TG) 55. The pixel array unit 50 is a pixel array unit in which a plurality of pixels 50a are arranged two-dimensionally in a matrix form in a row direction (X direction) and a column direction (Y direction), and is provided on the imaging surface 39a described above. A row selection line L1 and a row reset line L2 are wired to the pixel array unit 50 in the row direction and a column signal line L3 is wired in the column direction. Each pixel 50a is connected to the row selection line L1, the row reset line L2, and the column signal line L3. The TG 55 controls each unit on the basis of the control signal input from the control unit 41 of the processor device 12.

The pixel 50a includes a photodiode D1, an amplifier transistor M1, a pixel selection transistor M2, and a reset transistor M3. The photodiode D1 performs photoelectric conversion on incident ray, generates signal charge according to the amount of the incident ray, and accumulates the signal charge. The amplifier transistor M1 converts the signal charge accumulated in the photodiode D1 into a voltage value (pixel signal PS). The pixel selection transistor M2 is controlled by the row selection line L1, and the pixel signal PS generated by the amplifier transistor M1 is output to the column signal line L3. The reset transistor M3 is controlled by the row reset line L2 and the signal charge accumulated in the photodiode D1 is discarded (reset) to a power supply line.

The row scanning circuit 51 generates a row selection signal S1 and a reset signal S2 on the basis of the timing signal input from the TG 55. In a signal reading operation, the row scanning circuit 51 applies the row selection signal S1 to the row selection line L1 to cause the pixel signal PS of the pixel 50a connected to the row selection line L1 to be output to the column signal line L3. Further, in a resetting operation, the row scanning circuit 51 applies the reset signal S2 to the row reset line L2 to reset the pixels 50a connected to the row reset line L2.

Figure 6A:
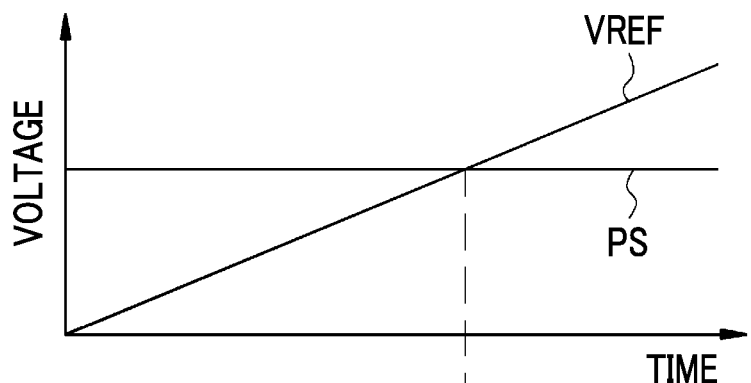
FIGS. 6A to 6C are diagrams illustrating an operation of a column ADC circuit.

The column ADC circuit 52 includes a comparator 52a, a counter 52b, and a reference signal generation unit 52c. The comparator 52a and the counter 52b are connected to each column signal line L3. The reference signal generation unit 52c generates a reference signal VREF that increases linearly with time, as illustrated in FIG. 6A, on the basis of a clock signal input from the TG 55. The pixel signal PS from the row selection line L1 and the reference signal VREF from the reference signal generation unit 52c are input to each comparator 52a.

Figure 6B:
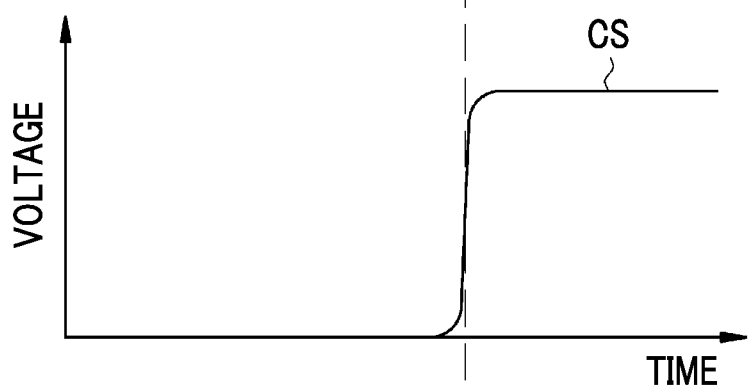
Figure 6C:
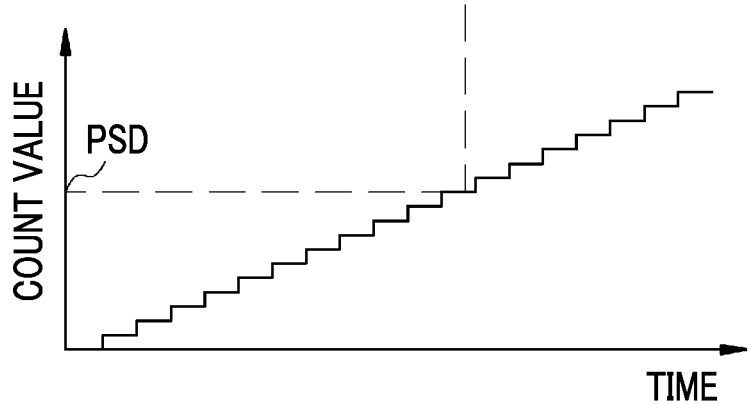

The comparator 52a compares the pixel signal PS with the reference signal VREF, and outputs a signal CS indicating a magnitude relationship between voltage values of the both signals, as illustrated in FIG. 6B. This output signal CS is input to the counter 52b. The counter 52b starts a counting operation with the start of an increase in the reference signal VREF, as illustrated in FIG. 6C, on the basis of the clock signal input from the TG 55. The counter 52b stops a counting operation in the event that voltage values of the pixel signal PS and the reference signal VREF match and the output signal CS is changed from a low level to a high level. A count value in the event that the counter 52b stops the counting operation corresponds to the pixel signal PS. This count value is a digital signal, and is output from the column ADC circuit 52 to the line memory 53 as a digitized pixel signal PSD.

The line memory 53 en bloc holds a pixel signal PSD of one row digitized by the column ADC circuit 52. The column scanning circuit 54 scans the line memory 53 on the basis of the timing signal input from the Tg 55 to cause the pixel signal PSD to be sequentially output from an output terminal Vout. The pixel signal PSD of one frame output from the output terminal Vout is the above-described imaging signal.

Figure 7:
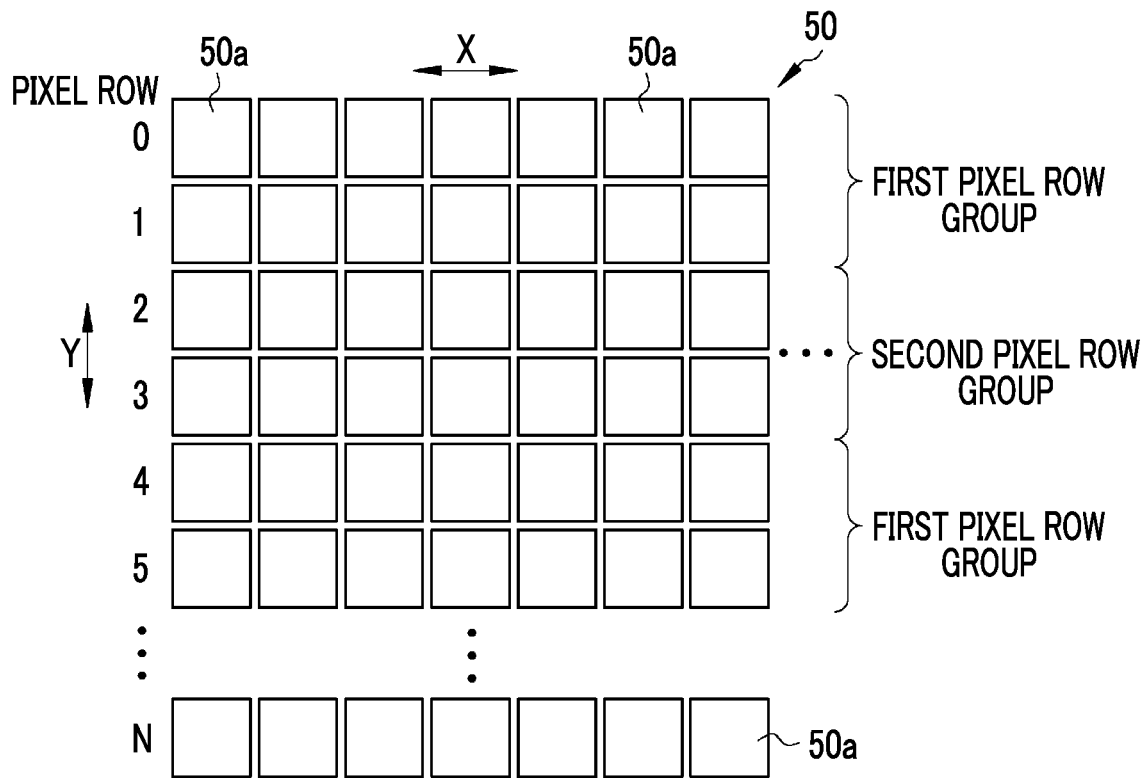
FIG. 7 is a diagram illustrating a configuration of a pixel array.

The TG 55 generates a timing signal on the basis of the imaging control signal input from the control unit 41 of the processor device 12. At the time of reading the imaging signal, a row selection signal S1 is applied while the row selection line L1 being sequentially selected by the row scanning circuit 51. Accordingly, signal reading is sequentially performed pixel row by pixel row from the first pixel row "0" to the last pixel row "N" illustrated in FIG. 7. Here, the pixel row refers to the pixels 50a in one row arranged in a row direction.

Further, a "sequential resetting scheme", a "batch resetting scheme", and a "partial resetting scheme" can be performed as a resetting scheme. In the sequential resetting scheme, a reset signal S2 is applied while the row reset lines L2 being sequentially selected by the row scanning circuit 51. Accordingly, in the sequential resetting scheme, the pixel rows are sequentially reset pixel row by pixel row from the first pixel row "0" to the last pixel row "N".

In the batch resetting scheme, all of the row reset lines L2 are selected by the row scanning circuit 51, and the reset signal S2 is applied to all of the row reset lines L2. Accordingly, all the pixel rows of the pixel array unit 50 are simultaneously reset en bloc.

In the partial resetting scheme, the reset signal S2 is applied to the row reset lines L2 of the pixel rows 2, 3, 6, 7, 10, 11, ..., N−1, and N which are some of all the pixel rows by the row scanning circuit 51. Accordingly, the pixel rows of a half of the pixel array unit 50 are simultaneously reset en bloc. Hereinafter, the pixel rows 0, 1, 4, 5, 8, 9, ..., N−3, and N−2 are referred to as a first pixel row group. Further, the pixel rows 2, 3, 6, 7, 10, 11, ..., N−1, and N are referred to as a second pixel row group.

Figure 8:
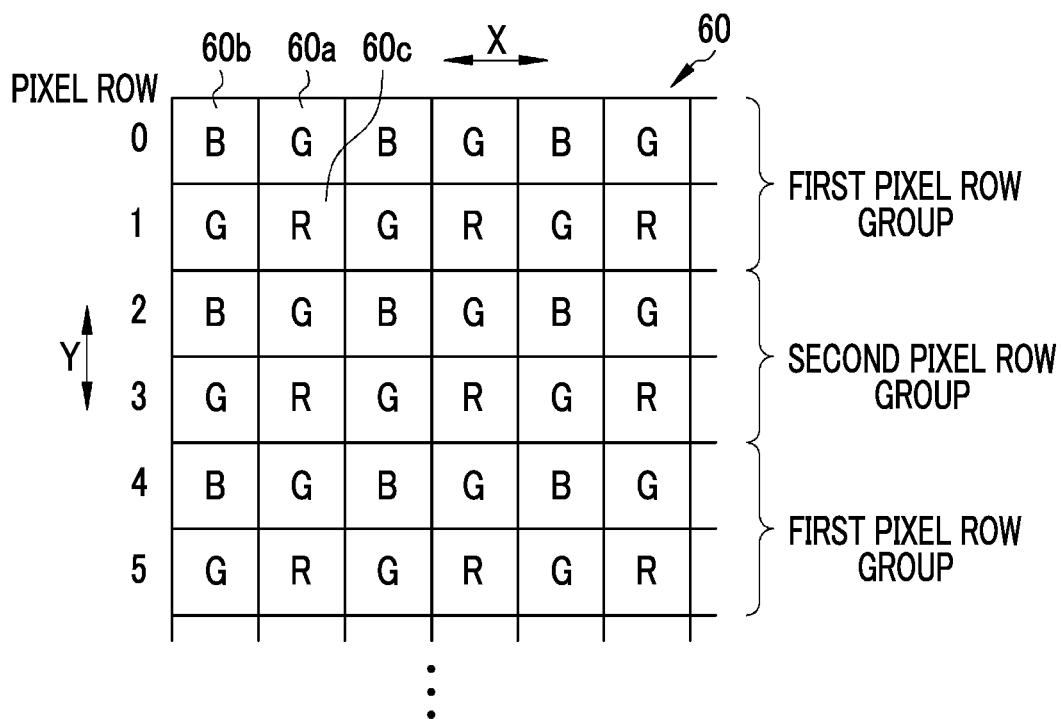
FIG. 8 is a diagram illustrating a configuration of a color filter array.

As illustrated in FIG. 8, a color filter array 60 is provided on the light incidence side of the pixel array unit 50. The color filter array 60 includes green (G) filters 60a, blue (B) filters 60b, and red (R) filters 60c. Any one of the filters is arranged on each pixel 50a. A color arrangement of the color filter array 60 is a Bayer array, G filters 60a are arranged on every other pixel in a pane, and the B filters 60b and the R filters 60c are arranged in a square lattice form in on the remaining pixels.

Figure 9:
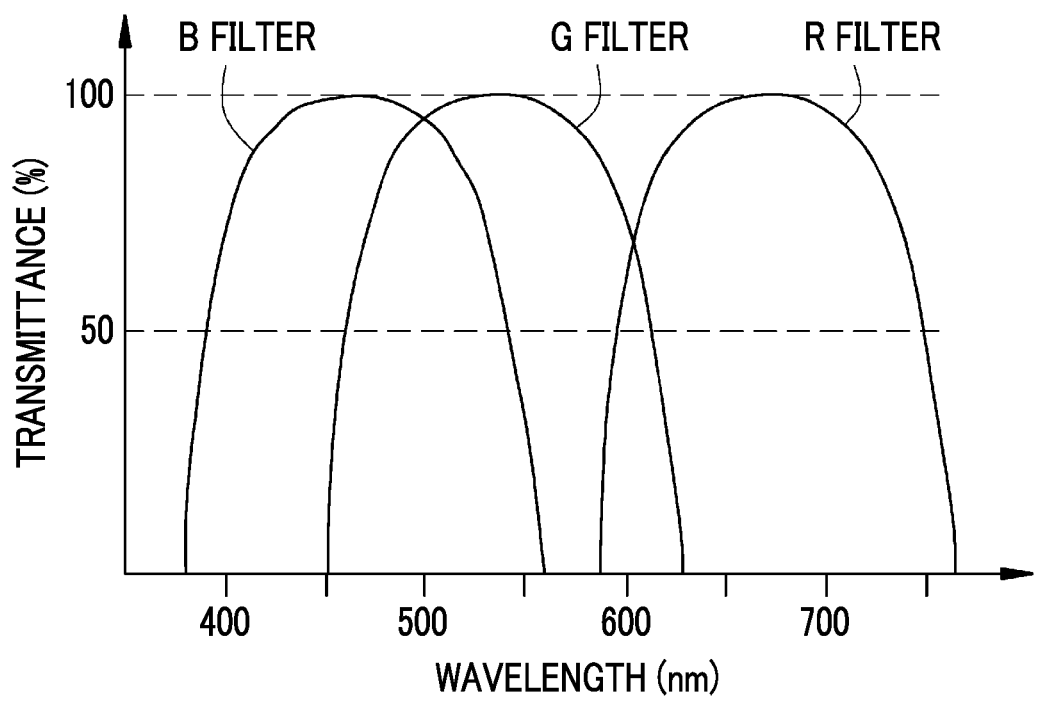
FIG. 9 is a graph illustrating spectral transmission characteristics of a color filter.

As illustrated in FIG. 9, the G filter 60a has a high transmittance for a wavelength range of about 450 to 630 nm. The B filter 60b has a high transmittance for a wavelength range of about 380 to 560 nm. The R filter 60c has a high transmittance for a wavelength range of about 580 to 760 nm. Hereinafter, the pixel 50a on which the G filter 60a is arranged is referred to as a G pixel, the pixel 50a on which the B filter 60b is arranged is referred to as a B pixel, and the pixel 50a on which the R filter 60c is arranged is referred to as an R pixel. Among these, a group of pixels most sensitive to different light absorption wavelength light, which will be described below, is a group of B pixels.

At the time of irradiation of the first illumination light, first blue laser light and a short wavelength side component of first fluorescence are incident on the B pixel, a main wavelength component of the first fluorescence is incident on the G pixel, and a long wavelength side component of the first fluorescence is incident on the R pixel. Similarly, at the time of irradiation of the second illumination light, second blue laser light and a short wavelength side component of second fluorescence are incident on the B pixel, a main wavelength component of the second fluorescence is incident on the G pixel, and a long wavelength side component of the second fluorescence is incident on the R pixel. Since an emission intensity of the first and second blue laser light is greater than that of the first and second fluorescence, most of the light incident on the B pixel is a component of the first blue laser light or the second blue laser light.

Thus, since the imaging element 39 is a single-plate type of color image sensor, the imaging signal is divided into G, B, and R pixel signals.

Figure 10:
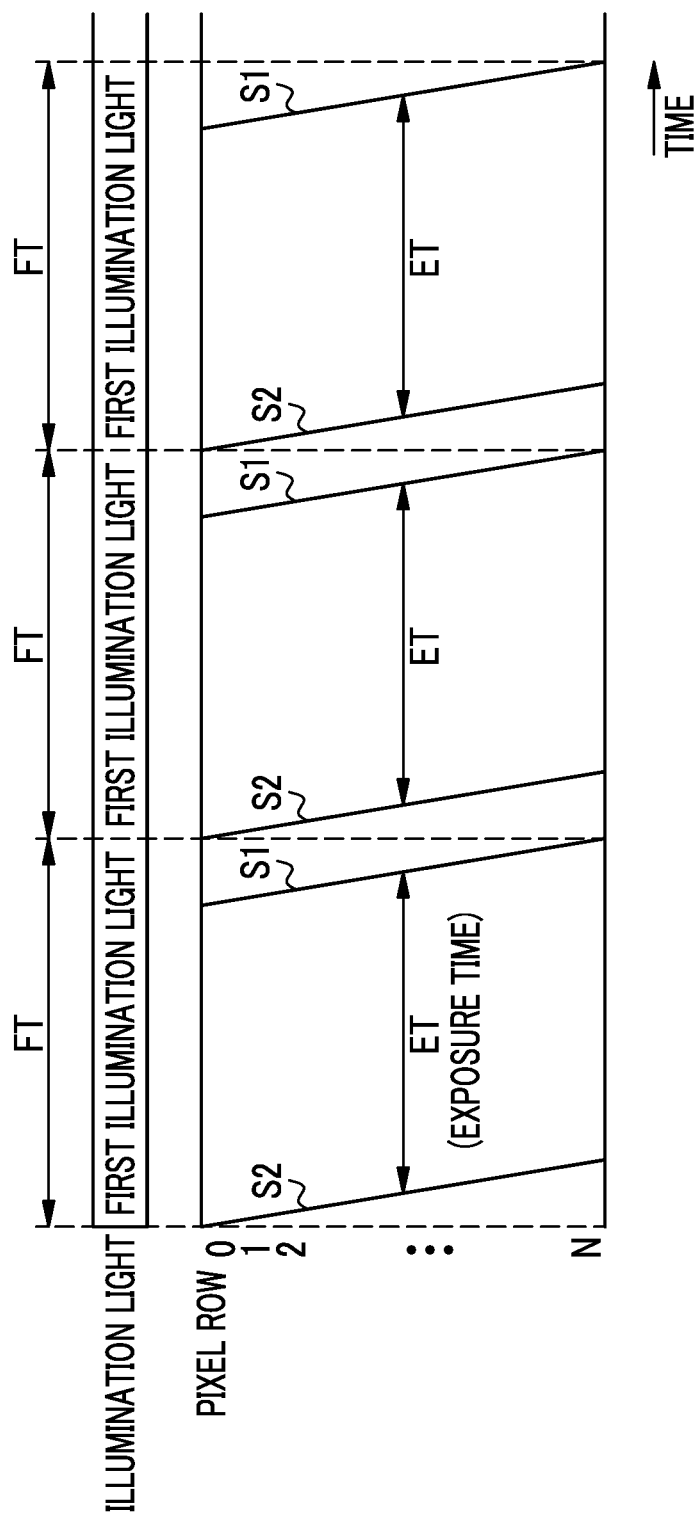
FIG. 10 is a diagram illustrating a driving timing in a normal observation mode.

Next, control of the control unit 41 according to an observation mode will be described. As illustrated in FIG. 10, in the normal observation mode, the control unit 41 controls the light source control unit 31 to turn on the first LD 30a and cause the first illumination light to be emitted from the illumination window 23 of the endoscope 11. In a state in which the first illumination light is emitted, the control unit 41 controls the imaging element 39 to drive the imaging element 39 in a rolling shutter scheme.

Specifically, first, in a sequentially resetting scheme, the control unit 41 sequentially resets the pixel rows pixel row by pixel row from the first pixel row "0" to the last pixel row "N". After an exposure time (ET) has elapsed from the start of this sequential reset has elapsed, the control unit 41 sequentially performs reading pixel row by pixel row from the first pixel row "0" to the last pixel row "N". As a result, an imaging signal corresponding to one frame is output from the imaging element 39. This driving in the rolling shutter scheme is repeatedly executed during the normal observation mode, and an imaging signal for one frame is obtained for one frame time FT (for example, 1/60 seconds).

Figure 11:
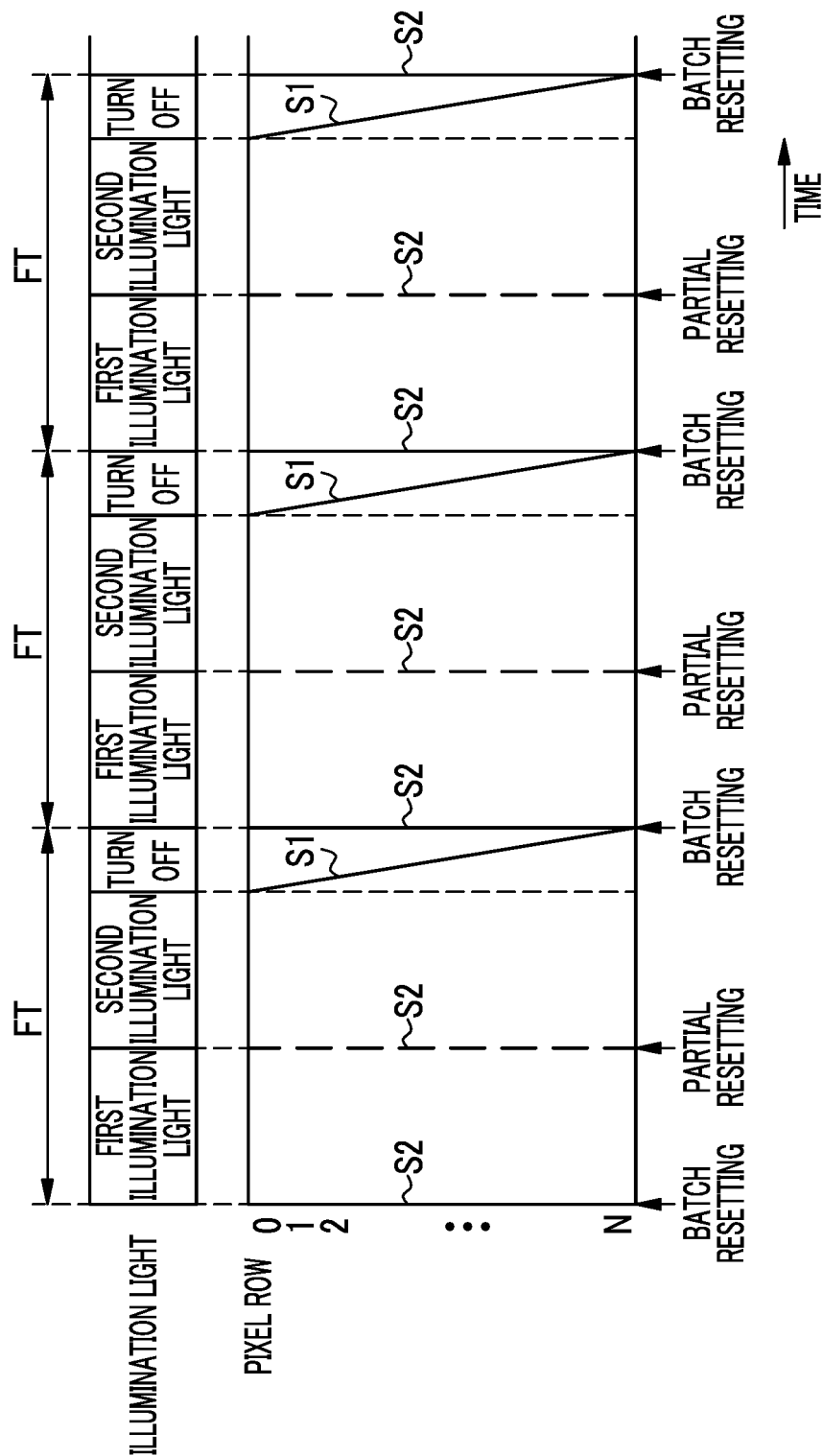
FIG. 11 is a diagram illustrating a driving timing in a special observation mode.

Assuming that the control unit 41 receives a mode switching operation signal for instructing switching from the normal observation mode to the special observation mode due to an operation of the mode changeover switch 22b during the normal observation mode, the control unit 41 controls the light source control unit 31 to sequentially turn on the first and second LDs 30a and 30b and cause the first and second illumination light to be sequentially emitted from the illumination window 23 of the endoscope 11 for each frame time FP, as illustrated in FIG. 11. After the irradiation of the second illumination light, a turn-off period in which the first and second LDs 30a and 30b are turned off is provided.

Specifically, first, all the pixel rows are simultaneously reset in a batch resetting scheme in a state in which the first illumination light is emitted from the illumination window 23 of the endoscope 11. After a time (ET/2) of a half of the above-described exposure time ET has elapsed from the execution of the batch resetting, the emission of the first illumination light stops, the second pixel row group described above is reset in the partial resetting scheme, and the illumination light is switched to the second illumination light. After a time (ET/2) of a half of the exposure time ET has elapsed from the start of irradiation of the second illumination light, the emission of the second illumination light stops.

Thereafter, both of the first and second LDs 30a and 30b enter a turn-off state. During this turn-off period, signal reading is sequentially performed pixel row by pixel row from the first pixel row "0" to the last pixel row "N" in a sequential reading scheme. As a result, the imaging signal of one frame is obtained. Since the first pixel row group among all the pixel rows is not reset, the exposure is performed by the first and second illumination light. Since one of the second pixel row groups is reset, the exposure is performed by only the second illumination light.

Hereinafter, the imaging signal from the first pixel row group is referred to as a first imaging signal, and the imaging signal from the second pixel row group is referred to as a second imaging signal. Further, respective pixel signals of G, B, and R included in the first imaging signal are referred to as a G1 pixel signal, a B1 pixel signal, and an R1 pixel signal. Respective pixel signals of G, B, and R included in the second imaging signal are referred to as a G2 pixel signal, a B2 pixel signal, and an R2 pixel signal.

Thus, in the special observation mode of this embodiment, since only signal reading of one frame is performed after the irradiation of the first and second illumination light, the reading time is the same as in the event that pixel decimation reading is performed after the irradiation of each illumination light as in the related art. Therefore, the special observation mode of this embodiment can be executed without a decrease in a frame rate from the normal observation mode.

As described above, in the special observation mode, the first and second imaging signals are input to the DSP 43. The DSP 43 performs a demosaicing process and an interpolation process to generate a set of B1, G1, and R1 pixel signals and a set of B2, G2, and R2 pixel signals per pixel.

Figure 12:
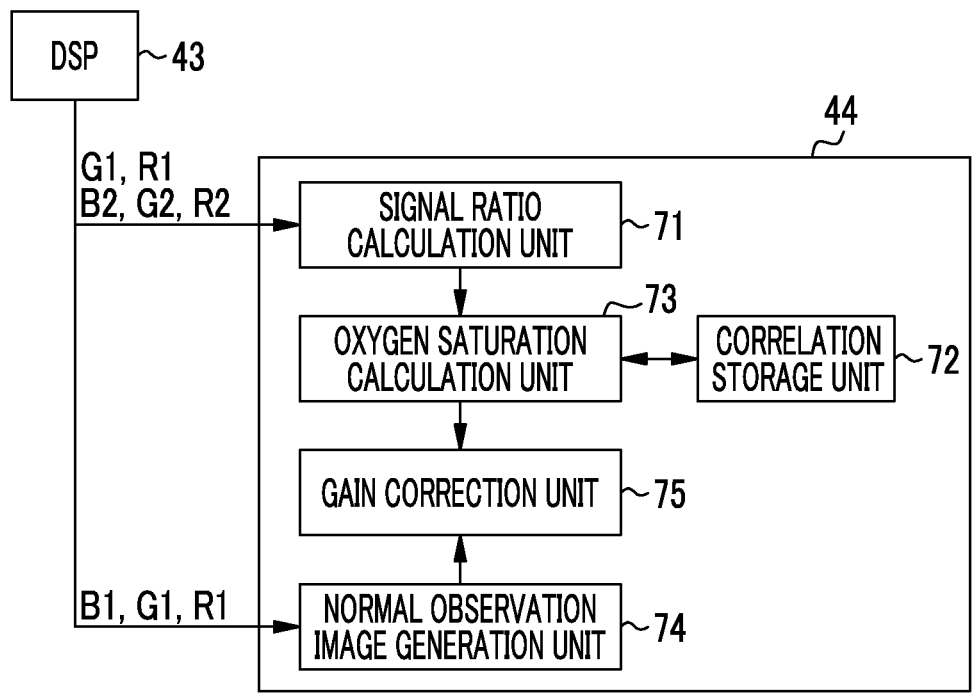
FIG. 12 is a block diagram illustrating a configuration of an image processing unit.

In FIG. 12, the image processing unit 44 of the processor device 12 includes a signal ratio calculation unit 71, a correlation storage unit 72, an oxygen saturation calculation unit 73, a normal observation image generation unit 74, and a gain correction unit 75.

The G1 pixel signal, the R1 pixel signal, the B2 pixel signal, the G2 pixel signal, and the R2 pixel signal in the first and second imaging signals input from the DSP 43 to the image processing unit 44 are input to the signal ratio calculation unit 71. The signal ratio calculation unit 71 calculates, for each pixel, a first subtraction value (G1−G2) obtained by subtracting the G2 pixel signal from the G1 pixel signal, and a second subtraction value (R1−R2) obtained by subtracting the R2 pixel signal from the R1 pixel signal. The signal ratio calculation unit 71 calculates, for each pixel, a signal ratio B2/(G1−G2) of the B2 pixel signal and the first subtraction value (G1−G2) and a signal ratio (R1−R2)/(G1−G2) of the second subtraction value (R1−R2) and the first subtraction value (G1−G2). Here, the first subtraction value (G1−G2) and the second subtraction value (R1−R2) correspond to a G pixel signal value and an R pixel signal value in the event that the irradiation with only the first illumination light is performed.

Figure 13:
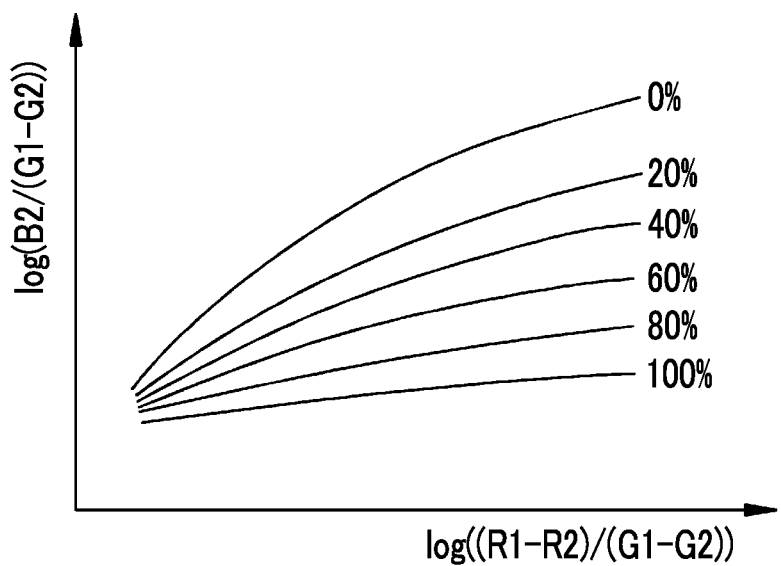
FIG. 13 is a graph illustrating a correlation of a signal ratio and an oxygen saturation.

The correlation storage unit 72 stores a correlation between the signal ratio B2/(G1−G2) and the signal ratio (R1−R2)/(G1−G2), and oxygen saturation. This correlation is stored as a two-dimensional table that defines an isopleths of the oxygen saturation on a two-dimensional space, as illustrated in FIG. 13. a position and a shape of the isopleths for the signal ratio B2/(G1−G2) and the signal ratio (R1−R2)/(G1−G2) are obtained by a physical simulation of light scattering in advance, and an interval of the respective isopleths varies according to the amount of blood (signal ratio (R1−R2)/(G1−G2)). The correlation between the signal ratio B2/(G1−G2) and the signal ratio (R1−R2)/(G1−G2), and the oxygen saturation is stored in a log scale.

Figure 14:
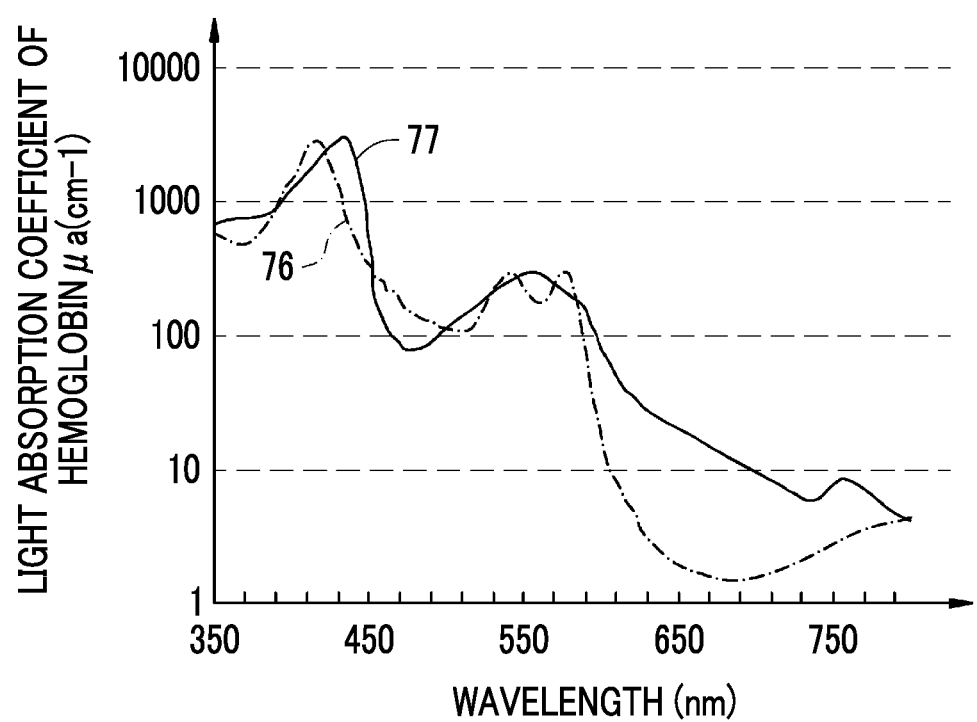
FIG. 14 is a graph illustrating light absorption coefficients of oxygenated hemoglobin and deoxygenated hemoglobin.

The above correlation is closely related to light absorption characteristics (an alternated long and short dash line 76) of oxygenated hemoglobin and light absorption characteristics of deoxygenated hemoglobin (solid line 77) illustrated in FIG. 14. The oxygen saturation can be calculated by using light with a wavelength at which a difference between a light absorption coefficient due to oxygenated hemoglobin and a light absorption coefficient of deoxygenated hemoglobin is great (different light absorption wavelength light), as in a central wavelength 473 nm of the second blue laser light. However, the B2 pixel signal mainly dependent on the second blue laser light depends greatly on the amount of blood as well as the oxygen saturation. On the other hand, the second subtraction value (R1−R2) corresponding to the R pixel signal value in the event that irradiation of only the first illumination light is performed mainly depends on the amount of blood.

Accordingly, by using values (the signal ratio B2/(G1−G2) and the signal ratio (R1−R2)/(G1−G2)) obtained by dividing the B2 pixel signal and the second subtraction value (R1−R2) by the first subtraction value (G1−G2) serving as a reference, it is possible to reduce dependency on the amount of blood and accurately obtain the oxygen saturation. Since an essential signal for calculation of the oxygen saturation is the B2 pixel signal, the oxygen saturation may be calculated from only the B2 pixel signal.

The oxygen saturation calculation unit 73 calculates, for each pixel, the oxygen saturation corresponding to the signal ratio B2/(G1−G2) and the signal ratio (R1−R2)/(G1−G2) calculated by the signal ratio calculation unit 71, by referring to the correlation stored in the correlation storage unit 72. The calculated value of the oxygen saturation is hardly smaller than 0% or hardly exceeds 100%. The oxygen saturation may be set to 0% in a case in which the calculated value is smaller than 0%, and the oxygen saturation may be set to 100% in a case in which the calculated value exceeds 100%.

The normal observation image generation unit 74 generates a normal observation image using the B1, G1, and R1 pixel signals included in the first imaging signal. Since the first imaging signal is an imaging signal for which the exposure is performed by the first and second illumination light, a normal observation image of which a luminance and an S/N ratio are the same as those in the normal observation mode is obtained by the normal observation image generation unit 74.

The gain correction unit 75 performs gain correction according to the oxygen saturation on each of the B1, G1, and R1 pixel signals constituting each pixel of the normal observation image. For example, in a pixel of which correction oxygen saturation is equal to or greater than 60%, a gain is set to "1" for any of B1, G1, and R1 pixel signals. On the other hand, in a pixel of which the correction oxygen saturation is smaller than 60%, the gain is set to less than "1" for the B1 pixel signal, and to "1" or greater for the G1 and R1 pixel signals. An image is generated using the B1, G1, and R1 pixel signals after gain correction. The normal observation image subjected to the gain correction in this way is an oxygen saturation image. In this oxygen saturation image, a high oxygen region (a region in which the oxygen saturation is 60 to 100%) has the same color as that of the normal observation image, whereas a low oxygen region (a region in which the oxygen saturation is 0 to 60%) is discolored to blue.

Figure 15:
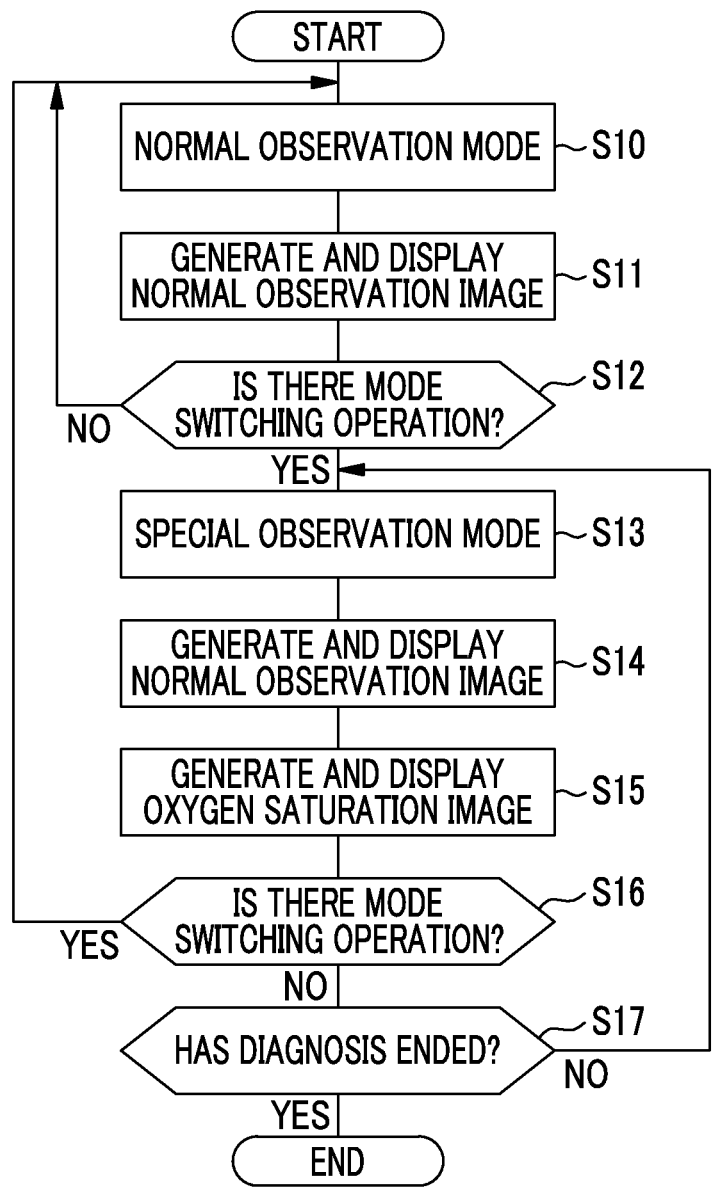
FIG. 15 is a flowchart illustrating an operation of the endoscope system.

Next, an operation of the endoscope system 10 will be described according to a flowchart of FIG. 15. First, an operator inserts the endoscope 11 into a living body, and observation of an observation part is performed in the normal observation mode (step S10). In this normal observation mode, in a state in which the observation part is irradiated with the first illumination light, the imaging element 39 is driven in a rolling shutter scheme, and an imaging signal is read from the imaging element 39 in every frame time, as illustrated in FIG. 10. The normal observation image is generated on the basis of this imaging signal by the image processing unit 44, and displayed on the monitor 14 (step S11). A display frame rate of the monitor 14 is the same as that of the imaging element 39, and the normal observation image displayed on the monitor 14 is updated for each frame time.

Assuming that an operator discovers a part in which a lesion is likely to be through observation in the normal observation mode and operates the mode changeover SW 22b and switching of the observation mode is performed (YES in step S12), transition to the special observation mode occurs (step S13). In the special observation mode, the observation part is irradiated with the first and second illumination light in order, and is turned off, as illustrated in FIG. 11. The imaging element 39 is concurrently reset at the start of the irradiation of the first illumination light, and only the second pixel row group is partially reset in the event that switching from the first illumination light to the second illumination light is performed. Signal reading for all the pixel rows is sequentially performed in the turn-off period, and the first and second imaging signals described above are output.

The first and second imaging signals are obtained for each frame time. Each time the first and second imaging signals are obtained, the normal observation image is generated on the basis of the first imaging signal by the image processing unit 44 and displayed on the monitor 14 (step S14), and the oxygen saturation image is generated on the basis of the first and second imaging signals by the image processing unit 44 and displayed on the monitor 14 (step S15). The normal observation image and the oxygen saturation image are, for example, simultaneously displayed side by side on a screen of the monitor 14.

The generation and the display of the normal observation image and the oxygen saturation image are repeatedly performed until the mode changeover SW 22b is operated again by the operator or an operation to end diagnosis is performed. Assuming that the mode changeover SW 22b is operated (YES in step S16), returning to the normal observation mode occurs (step S10) and the same operation is performed. On the other hand, assuming that the operation to end the diagnosis is performed without the mode changeover SW 22b being operated (YES in step S17), the operation of the endoscope system 10 ends.

Although the signal reading is sequentially performed pixel row by pixel row the first pixel row "0" to the last pixel row "N" after the first and second illumination light is radiated in the special observation mode in the above embodiment, the pixel rows in the first pixel row group may be sequentially read, and then, the pixel rows in the second pixel row group may be sequentially read. Conversely, the pixel rows in the second pixel row group may be sequentially read, and then, the pixel rows in the first pixel row group may be sequentially read.

Although the first illumination light is the light having the first blue laser light and the second illumination light is the light having the second blue laser light (different light absorption wavelength light) in the above embodiment, the first illumination light may be the light having the second blue laser light (different light absorption wavelength light) and the second illumination light may be the light having the first blue laser light. The oxygen saturation may be calculated on the basis of the signal ratio (B1−B2)/G2 and the signal ratio R2/G2.

Although the oxygen saturation image is generated by performing image processing on the normal observation image on the basis of the oxygen saturation in the above embodiment, an image from information on the oxygen saturation may be the oxygen saturation image.

Although the batch resetting is performed at the start of the irradiation of the first illumination light as illustrated in FIG. 11 in the above embodiment, the resetting may be performed in a sequential resetting scheme in the turn-off period before the start of the irradiation of the first illumination light without performing the batch resetting. For example, in the turn-off period, the pixel rows immediately after the signal has been read may be sequentially reset.

Figure 16:
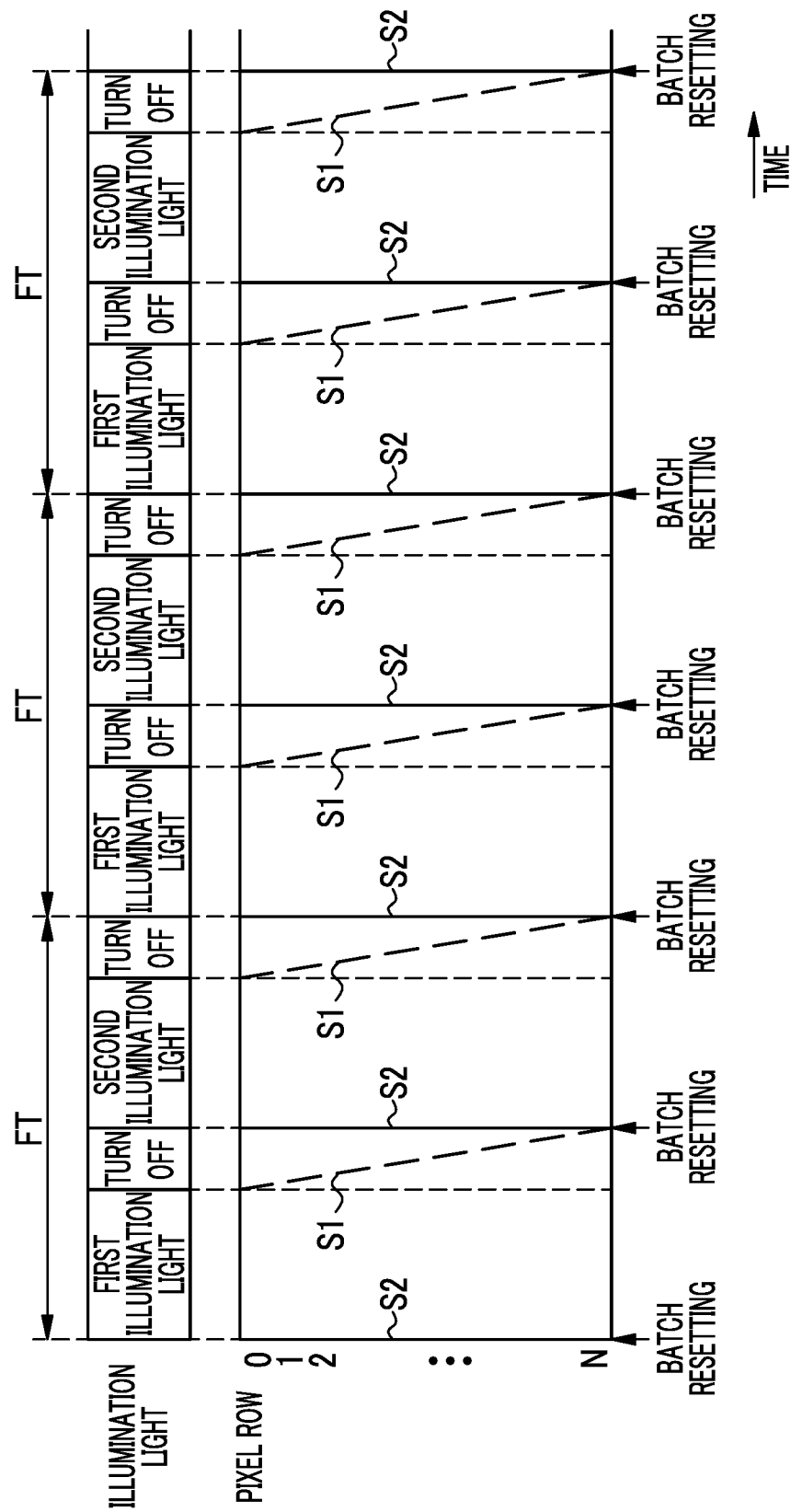
FIG. 16 is a diagram illustrating a driving timing in a second imaging scheme.

Although the light source device 13 and the imaging element 39 are driven in an imaging scheme (hereinafter referred to as a first imaging scheme) illustrated in FIG. 11 in the special observation mode in the above embodiment, the light source device 13 and the imaging element 39 may be driven in the imaging scheme of the related art (hereinafter referred to as a second imaging scheme) illustrated in FIG. 16.

In the second imaging scheme, the first and second illumination light is alternately radiated over the turn-off period, and the signal reading is performed in a decimation reading scheme in each turn-off period. Further, all of the pixel rows are simultaneously reset en bloc in the batch resetting scheme at the start of the irradiation of each illumination light. In the signal reading, for example, only the first pixel row group described above from the pixel array unit 50 is read, such that pixel decimation is performed. A frame rate of the second imaging scheme is the same as that of the first imaging scheme.

In the second imaging scheme, the normal observation image is generated on the basis of the imaging signal read after the irradiation of the first illumination light. The oxygen saturation image is generated on the basis of the imaging signal read after the irradiation of the first illumination light and the imaging signal read after the irradiation of the second illumination light. The oxygen saturation image may be generated using only the imaging signal read after the irradiation of the second illumination light. In the second imaging scheme, since the normal observation image is generated on the basis of the imaging signal obtained by the first illumination light, similar to the normal observation image in the normal observation mode, for example, the same white balance processing as that in the normal observation mode can be performed by the DSP 43.

Further, in the first imaging scheme, the brightness and the S/N ratio of the normal observation image are improved, but the exposure time is longer than that in the second imaging scheme, and subject blur, camera shake, or the like easily occurs. Therefore, the first imaging scheme and the second imaging scheme may be switched according to the brightness of the specimen.

Figure 17:
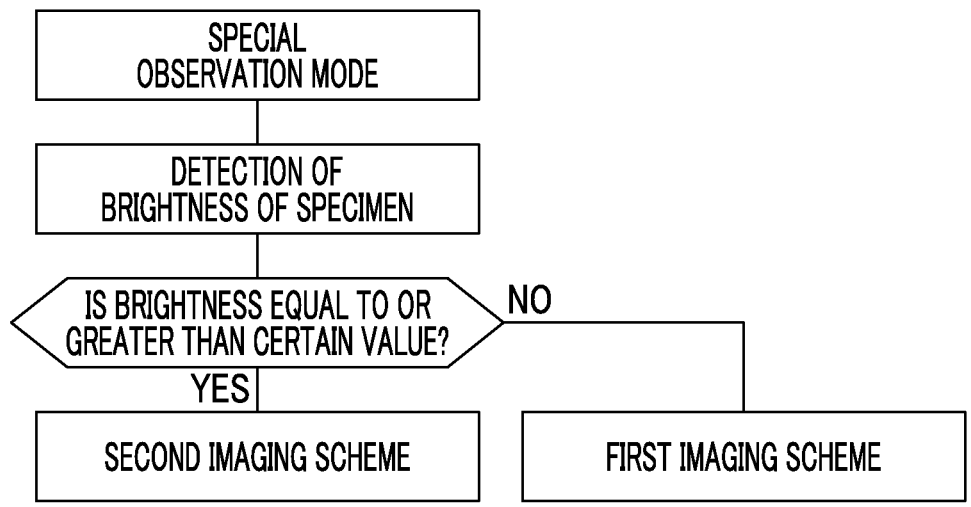
FIG. 17 is a flowchart illustrating a method of switching between first and second imaging schemes.

Specifically, after the observation mode is switched from the normal observation mode to the special observation mode, the brightness of the specimen is detected, as illustrated in FIG. 17. The brightness of this specimen is calculated by the DSP 43 on the basis of the imaging signal. For example, by calculating an average luminance value from the imaging signal for one frame, the brightness of the specimen is obtained. That is, the DSP 43 corresponds to a brightness detection unit. In this luminance detection, any of the imaging signal in the first imaging scheme and the imaging signal in the second imaging scheme may be used.

After the brightness of the specimen is detected, the second imaging scheme is selected in a case in which the brightness is equal to or greater than a certain value, and the first imaging scheme is selected in a case in which the brightness is smaller than the certain value. The brightness of the specimen is calculated in the normal observation mode, and in the event that the observation mode is switched to the special observation mode, the imaging scheme may be selected on the basis of the brightness calculated in the normal observation mode.

Further, it is determined whether an S/N ratio of the imaging signal is low, instead of the brightness of the specimen, and a gain equal to or greater than a certain value is necessary in the DSP 43 or the like. The first imaging scheme may be selected in a case in which the gain equal to or greater than a certain value is necessary, and the second imaging scheme may be selected in a case in which the gain equal to or greater than a certain value is not necessary.

Further, in the second imaging scheme, the resetting may also be performed in the sequential resetting scheme in the turn-off period without the batch resetting being performed at the start of the irradiation of each illumination light.

Further, in the second imaging scheme, signal reading may be performed after the irradiation of the first illumination light, and then, signal reading may be performed after the irradiation of the second illumination light is performed without performing the resetting on any of all the pixel rows. In this case, it is preferable to change the pixel row on which decimation reading is performed through signal reading after irradiation of the first illumination light and signal reading after irradiation of the second illumination light.

For example, decimation reading for reading only the first pixel row group in a turn-off period after the irradiation of the first illumination light is performed, and decimation reading for reading only the first pixel row group in a turn-off period after the irradiation of the second illumination light is performed. Accordingly, the first imaging signal is read from the first pixel row group on which the exposure is performed by the first illumination light, and the second imaging signal is read from the second pixel row group on which the exposure is performed by the first and second illumination light.

By generating the normal observation image on the basis of the second imaging signal, the luminance and the S/N ratio are improved, similar to the above embodiment. The oxygen saturation image may be generated on the basis of the first and second imaging signals. In a case in which the first illumination light is light having a different light absorption wavelength light, it is also possible to generate the oxygen saturation image on the basis of only the first imaging signal.

Although the primary color type of color filter array 60 is used in the embodiment, a complementary color filter array may be used in place of the primary color type of color filter array 60.

Although the first and second illumination light is generated by irradiating the phosphor 36 with the first and second laser light emitted from the first and second LDs 30a and 30b in the above embodiment, the first and second illumination light may be generated by a white light source such as a xenon lamp and a wavelength selective filter, as disclosed in JP2013-165776A. Further, it is possible to generate the first and second illumination light using a light-emitting diode (LED) (for example, three types of LEDs that emit R, G, and B light) and a wavelength selection filter.

Although the oxygen saturation image is generated as the special observation image by using the white light as the first illumination light and special light including light with a high light absorption coefficient of blood hemoglobin as the second illumination light in the above embodiment, a blood vessel emphasized observation image in which a blood vessel of a biological tissue surface layer is emphasized may be generated as the special observation image by using narrowband light with a high light absorption coefficient of blood hemoglobin (for example, violet narrowband light with a central wavelength of 405 nm) as the second illumination light.

Although the light source device and the processor device are separate entities in the embodiment, the light source device and the processor device may be configured as one device.

Figure 18:
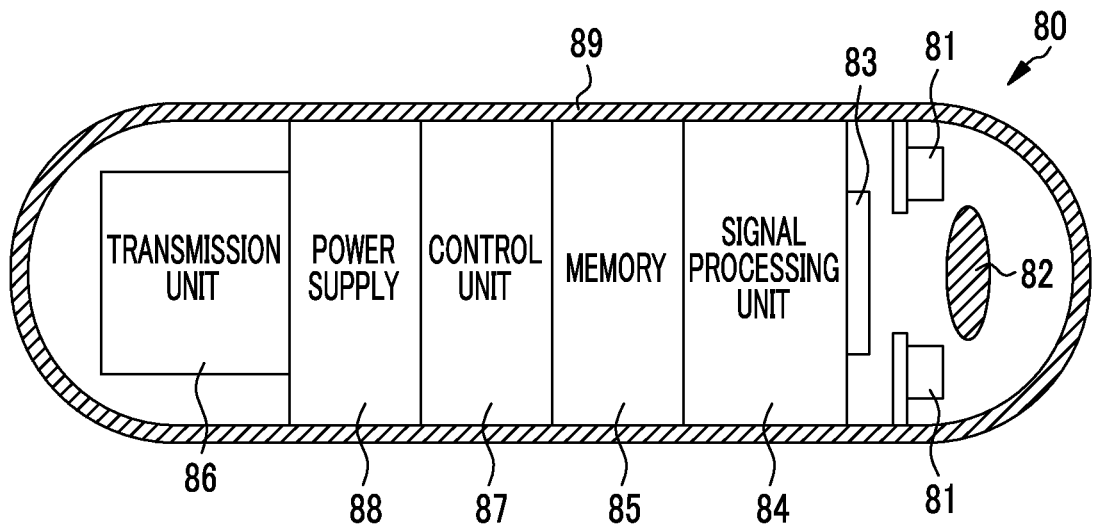
FIG. 18 is a diagram illustrating a configuration of a capsule endoscope.

The present invention is applicable to a capsule endoscope that captures images while passing through the inside of a digestive tract and transfers the captured images to a recording device. For example, as illustrated in FIG. 18, the capsule endoscope 80 includes an illumination unit 81, a lens 82, an imaging element 83, a signal processing unit 84, a memory 85, a transmission unit 86, a control unit 87, a power supply 88, and a capsule housing 89 that accommodates these.

The illumination unit 81 includes an LED and a wavelength selection filter, and irradiates a specimen with the first and second illumination light described above. The imaging element 83 is a CMOS type, and images, through the lens 82, reflected light from the specimen illuminated with the first and second illumination light, and outputs the first and second imaging signals described above. The signal processing unit 84 performs, on the first and second imaging signals, signal processing, which is performed by the DSP 43 and the image processing unit 44 in the above embodiment, to generate a normal observation image and an oxygen saturation image. The memory 85 stores each image. The transmission unit 86 wirelessly transmits each image stored in the memory 85 to an external recording device (not illustrated). The control unit 87 controls each unit.

The first and second imaging signals may be transmitted from the transmission unit 86 to an external device (not illustrated), and the external device may perform generation of the normal observation image and the oxygen saturation image.

Further, the present invention is also applicable to a fiberscope that guides reflected light of illumination light from an observation part with an image guide, or an endoscope system using an ultrasound endoscope in which an imaging element and an ultrasonic transducer are built into a distal end portion of the ultrasound endoscope.

EXPLANATION OF REFERENCES

10 endoscope system
11 endoscope
12 processor device
13 light source device
30a first laser diode
30b second laser diode
35 light guide
36 phosphor
39 imaging element
41 control unit
50 pixel array unit
50a pixel

What is claimed is:
1. An endoscope system, comprising:
an illumination unit including at least one light source that irradiates a specimen sequentially with first and second illumination light having different spectral characteristics;

an endoscope including a CMOS type imaging element that images the specimen that is illuminated by the illumination unit using a plurality of pixel rows arranged in a column direction, the imaging element being a color image sensor;
a processor configured to:
cause the illumination unit and the imaging element to execute a first imaging scheme for resetting some of the plurality of pixel rows en bloc after the specimen is irradiated with the first illumination light from the illumination unit, turn off the illumination unit after the specimen is irradiated with the second illumination light from the illumination unit, and perform signal reading from all of the pixel rows; and
generate a normal observation image on the basis of a first imaging signal read from the pixel row exposed by the first and second illumination light without being subjected to the resetting, and generate a special observation image on the basis of a second imaging signal read from the pixel row at least subjected to the resetting and exposed by only the second illumination light.

2. The endoscope system according to claim 1, wherein the imaging element includes a color filter array in a Bayer array, and
the processor is further configured to perform the resetting on a half of the plurality of pixel rows.

3. The endoscope system according to claim 1, wherein the first illumination light or the second illumination light includes different light absorption wavelength light for which a light absorption coefficient differs between oxygenated hemoglobin and deoxygenated hemoglobin, and
the processor is further configured to generate an oxygen saturation image including information on oxygen saturation as the special observation image.

4. The endoscope system according to claim 3, wherein the processor is further configured to calculate the oxygen saturation on the basis of the first and second imaging signals, and performs image processing on the normal observation image on the basis of the oxygen saturation to generate the oxygen saturation image.

5. The endoscope system according to claim 1, wherein the processor is further configured to cause the illumination unit and the imaging element to execute a second imaging scheme for turning off the illumination unit and performing signal reading after the specimen is irradiated with the first illumination light from the illumination unit, and turning off the illumination unit and performing signal reading after the specimen is irradiated with the second illumination light from the illumination unit.

6. The endoscope system according to claim 5, wherein the processor is further configured to perform the signal reading after the irradiation of the first illumination light, and then, radiates the second illumination light without resetting any of the plurality of pixel rows at the time of execution of the second imaging scheme.

7. The endoscope system according to claim 6, wherein the processor is further configured to perform the signal reading from some of the plurality of pixel rows through decimation reading at the time of execution of the second imaging scheme.

8. The endoscope system according to claim 7, wherein the processor is further configured to change the pixel row on which the decimation reading is performed through signal reading after irradiation of the first illumination light and signal reading after irradiation of the second illumination light at the time of execution of the second imaging scheme.

9. The endoscope system according to claim 5, further comprising:
a brightness detection unit that detects brightness of the specimen,
wherein the processor is further configured to cause the first imaging scheme to be executed in a case in which the brightness is smaller than a certain value, and the second imaging scheme to be executed in a case in which the brightness is equal to or greater than the certain value.

10. A processor device of an endoscope system, the endoscope system including an illumination unit including at least one light source that irradiates a specimen sequentially with first and second illumination light having different spectral characteristics, and an endoscope including a CMOS type imaging element that images the specimen illuminated by the illumination unit using a plurality of pixel rows arranged in a column direction, the processor device comprising:
a processor configured to:
cause the illumination unit and the imaging element to execute a first imaging scheme for resetting some of the plurality of pixel rows en bloc after the specimen is irradiated with the first illumination light from the illumination unit, turning off the illumination unit after the specimen is irradiated with the second illumination light from the illumination unit, and performing signal reading from all of the pixel rows, the imaging element being a color image sensor; and
generate a normal observation image on the basis of a first imaging signal read from the pixel row exposed by the first and second illumination light without being subjected to the resetting, and generates a special observation image on the basis of a second imaging signal read from the pixel row at least subjected to the resetting and exposed by only the second illumination light.

11. A method of operating an endoscope system, the endoscope system including an illumination unit including at least one light source that irradiates a specimen sequentially with first and second illumination light having different spectral characteristics, and an endoscope including a CMOS type imaging element that images the specimen illuminated by the illumination unit using a plurality of pixel rows arranged in a column direction, the method comprising:
a first step in which a processor causes the illumination unit and the imaging element to execute a first imaging scheme for resetting some of the plurality of pixel rows en bloc after the specimen is irradiated with the first illumination light from the illumination unit, turning off the illumination unit after the specimen is irradiated with the second illumination light from the illumination unit, and performing signal reading from all of the pixel rows, the imaging element being a color image sensor; and
a second step in which the processor generates a normal observation image on the basis of a first imaging signal read from the pixel row exposed by the first and second illumination light without being subjected to the resetting, and generates a special observation image on the basis of a second imaging signal read from the pixel row at least subjected to the resetting and exposed by only the second illumination light.

\* \* \* \* \*